United States Patent [19]

Spierer

[11] Patent Number: 4,477,776
[45] Date of Patent: Oct. 16, 1984

[54] APPARATUS AND PROCESS FOR FLUX LEAKAGE TESTING USING TRANSVERSE AND VECTORED MAGNETIZATION

[75] Inventor: Edward Spierer, Belle Harbor, N.Y.

[73] Assignee: Magnetic Analysis Corporation, Mount Vernon, N.Y.

[21] Appl. No.: 317,467

[22] Filed: Nov. 2, 1981

[51] Int. Cl.³ .................. G01N 27/72; G01R 33/12
[52] U.S. Cl. ................................ 324/227; 324/232; 324/242
[58] Field of Search .............. 324/232, 225, 219, 220, 324/221, 226, 227, 239–243

[56] References Cited

U.S. PATENT DOCUMENTS

| | | | |
|---|---|---|---|
| 3,080,507 | 3/1963 | Wickerham et al. | 324/225 |
| 3,287,632 | 11/1966 | Tompkins | 324/232 |
| 3,535,624 | 10/1970 | Wood | 324/226 |
| 3,538,433 | 11/1970 | Wood et al. | 324/232 |

Primary Examiner—Gerard R. Strecker
Assistant Examiner—Walter E. Snow
Attorney, Agent, or Firm—Pennie & Edmonds

[57] ABSTRACT

An apparatus and process for detecting both longitudinal and circumferential defects in a test object relatively rotating and longitudinally translating with respect to a test apparatus is disclosed. Means are provided for producing a transverse magnetic field in the object. Additional means provide a longitudinal magnetic field intersecting the transverse magnetic field in the first test region of the object. Magnetic sensing means then provide output signals in response to the presence of flux leakage from the test region due to defects. Circuits responsive to the output signals are provided for indicating flaws.

8 Claims, 11 Drawing Figures

APPARATUS AND PROCESS FOR FLUX LEAKAGE TESTING USING TRANSVERSE AND VECTORED MAGNETIZATION

TECHNICAL FIELD

This invention relates to flux leakage testing of materials. More particularly, it relates to an apparatus and process for performing tests for both longitudinal and transverse defects during a single test operation.

BACKGROUND ART

When a metallic member is magnetized, a leakage flux is generated at any point where a discontinuity, flaw, or defect in the material exists. The quantity of leakage flux, and therefore the sensitivity of sensing devices to the defect is dependent upon the relative orientation of the defect and the field. If narrow cracks are parallel to the magnetic field, virtually no flux leakage is generated and the defect may not be detected.

The detection of all defects regardless of orientation has generally required that the object under test be inspected more than once, as is taught in U.S. Pat. No. 3,287,632 to Tompkins. The apparatus of Tompkins applies magnetic flux in two directions relative to a tubular member separate and apart from one another to avoid interference and inaccurate data resulting from mingling and vector addition of magnetic field (see column 1, lines 66–70).

Complex apparatus for detecting defects at various orientations have been developed. U.S. Pat. No. 3,994,911 to Tornblom discloses an apparatus in which a multiphase generator is used to generate a traveling magnetic field such as a rotating or linearly traveling field in the body being tested and in which means are provided to sense any assymetry in the magnetic field which results from eddy currents induced in the object. A Y-connected multiphase generator is used to feed a first plurality of Y-connected transducer coils comprising at least one coil per phase. A second plurality of Y-connected transducer coils connected to the multiphase generator induces a moving field in the body in a direction opposite to that of the moving field generated by the first coils. Still more coils are required to detect variations in the electric field generated when faults and irregularities in the body being tested are encountered.

A similar apparatus is disclosed in U.S. Pat. No. 3,855,530 to Fuji et al. A metal defect detecting apparatus is disclosed comprising a cross-shaped magnetic core assembly prepared from two pairs of magnetic pole members which provide two pairs of magnetic poles intersecting each other at right angles, a first and second coil wound about the two pairs of magnetic pole members, and a power supply for supplying the first coil with single phase alternating current of positive half wave and the second with single phase alternating current of negative half wave, thus alternately supplying each of the two magnetic fluxes in perpendicularly intersecting directions. A leakage magnetic flux representing a vector sum of the magnetic fluxes occurs when a defect obliquely intersects either of the fluxes (see column 3, line 65 to column 4, line 19). This apparatus is intended to be used with magnetized powders.

Various arrangements using perpendicular magnetic fields have been exploited in the field of eddy current testing. For example, U.S. Pat. No. 3,495,166 discloses eddy current crack detection systems using crossed coils with fields perpendicular to each other and parallel to the surface of a part. Variations in conductivity, permeability, lift-off, and surface conditions produce substantially no output from the bridge detector circuit network, but defects produce a large output.

Another eddy current detection apparatus is disclosed in U.S. Pat. No. 4,134,062 to Woodbury. This device is designed primarily for rapid scanning of the interior walls of tubes or holes in metal parts in order to detect faults such as fissures, cracks, or other defects. It incorporates sensing transformer elements in the probe differentially connected so as to cancel out and reject from the sensing circuit the effects of false responses due to transitional positioning of the probe, such as those that can occur when the probe is being inserted and removed from a test probe (see column 1, lines 43 to 50).

While the detection of these defects having various orientations within the object under test may be accomplished using these and possibly other prior art systems, outputs are generally not developed which are indicative of the nature, orientation and size of the defect unless more than one test operation is performed. In addition it is difficult to distinguish between signals generated by defects and those generated by normal variations in the contour of the part such as changes in diameter at shoulders.

DISCLOSURE OF THE INVENTION

The present invention provides a process and apparatus which may be used to detect both longitudinal and transverse defects in a test object which is of circular cross section typically cylindrically shaped and moving longitudinally and rotationally with respect to the test apparatus. A means for producing a transverse magnetic field in the object is provided. Means for producing a longitudinal magnetic field which intersects the transverse field in a first test region of the object is also provided. A circuit responsive to output signals provided by a magnetic sensing means which responds to the presence of leakage flux from the test region indicates the presence of flaws in the object. The presence of both a transverse and a longitudinal field produces a vectored field diagonally in the test object. Means are provided to continuously and rapidly vary the intensity or direction of the longitudinal magnetic field and flux leakage will occur for both longitudinal and transverse defects.

The sensing means however may be of a type such as that disclosed in U.S. Pat. No. 3,940,690 to Suhr which is strongly preferentially sensitive to magnetic flux only along the line of the metal insert around which the sensing coil is wound. Proper orientation of such a sensor located adjacent the region in which the magnetic fields intersect will render this sensor sensitive only to transverse defects.

An additional sensor may be supplied for the detection of flux leakage from longitudinal defects. This sensor is advantageously located adjacent a region of the test object exposed only to the transverse magnetic field. A second circuit means responsive to output signals from this second sensor provides an indication of longitudinal defects in the test object.

It is preferred that the intensity of the transverse magnetic field be just below that necessary to cause saturation of the test object. The longitudinal or vectoring field, however, need not be nearly as intense, a field of moderate intensity generally being sufficient.

In order to properly estimate the size and therefore the severity of defects, it is necessary that the intensity of the transverse magnetic field in the material be substantially constant as wall thickness changes with position along the test object. When wall thickness change is due to an external change of diameter, the change in the distance from magnetic pole pieces to the test object will automatically compensate to a certain extent for the change in wall thickness. For best results however an apparatus according to the invention is provided with a means for programming the intensity of the transverse magnetic field to provide a substantially constant field in the test object during the duration of the test. To aid in programming, a means for determining the strength of the transverse field in the test object is provided. A means for providing an indication when the intensity falls outside a predetermined range of values may be provided to assure that the corrections in field intensity resulting from the programming are adequate.

Under normal test conditions the test object is rotated and longitudinally moved relative to the test apparatus. If the external diameter of the test object changes due to the presence of a shoulder, a change in flux leakage will be produced. This change will produce a signal which may be interpreted as indicating the presence of a flaw. Such signals can be readily distinguished from valid flaw indications if the test object is permitted to continue to rotate but its longitudinal motion is halted. Under these circumstances, flaws continue to produce output signals while a properly machined uniform shoulder will not. Therefore, means are advantageously provided to halt the longitudinal motion of the test object with respect to the test apparatus.

DETAILED DESCRIPTION OF THE INVENTION

Figure 1:
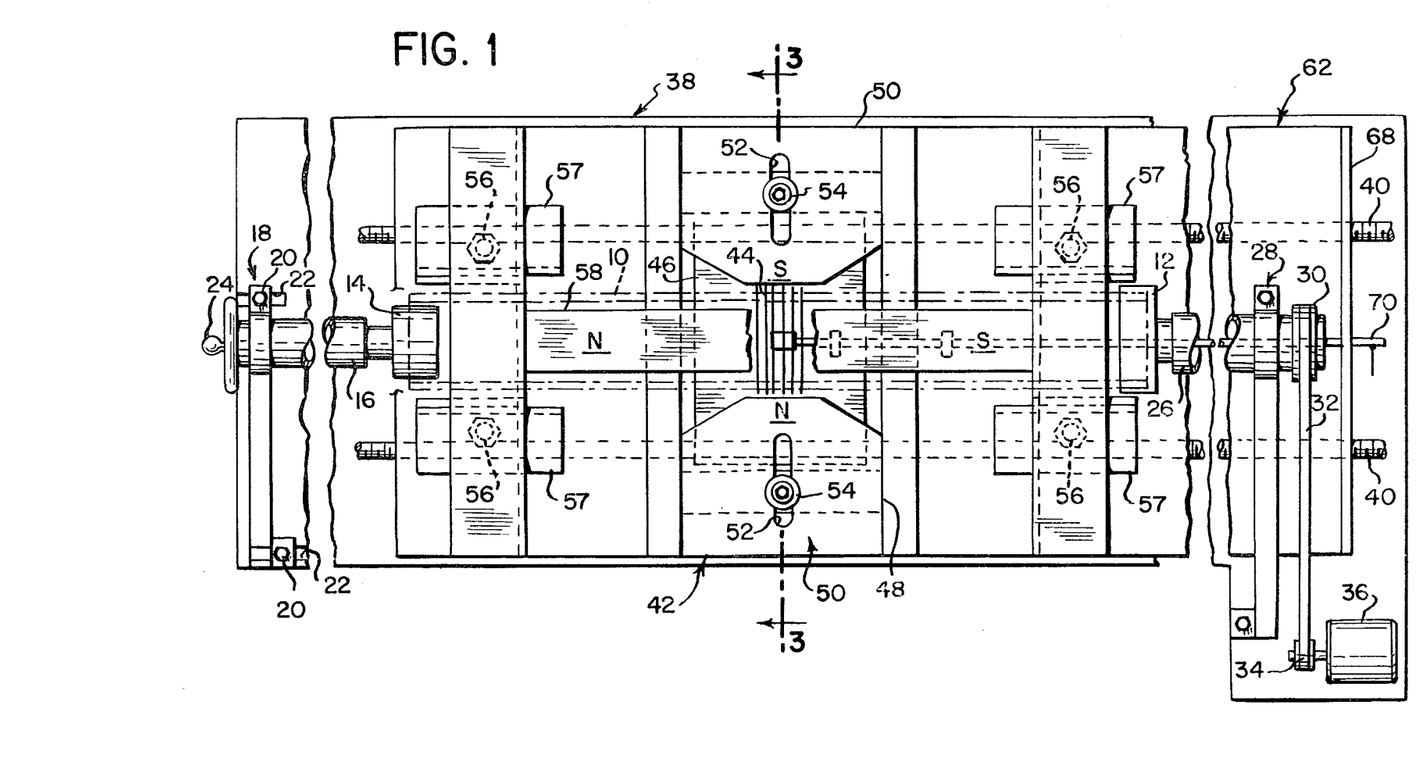
FIG. 1 is a plan view of an apparatus according to the invention.

Rotary flux leakage testing is most useful with object of circular cross section. It is particularly useful with cylindrical test objects which move relatively rotationally and longitudinally with respect to the test apparatus or more particularly the active test components of that apparatus. In FIG. 1 a plan view of an apparatus according to the invention illustrates a test object 10 (shown in dotted lines) supported at the right by external clamping means 12 which may comprise a set of jaws of the type commonly used in an engine lathe. Object 10 supported at the left by an internal rotatable support 14 connected to shaft 16 which is rotatably mounted in a structure 18 similar to the tail stock of a lathe. Coarse positioning of structure 18 in the longitudinal direction of object 10 is provided by loosening one or more bolts 20 permitting sliding in slots 22. Fine positioning is provided by rotating handle 24. Structure 18 is of a conventional tail stock structure as is well known in the art.

External clamping means 12 is connected to shaft 26 which is rotatably mounted in a journal bearing in structure 28. A pulley 30 mounted on the portion of shaft 26 external to structure 28 is connected by a drive belt 32 to a pulley 34 mounted on the rotating shaft of motor 36. Activation of motor 36 therefore results in the rotation of external clamping means 12 and test object 10.

Figure 2:
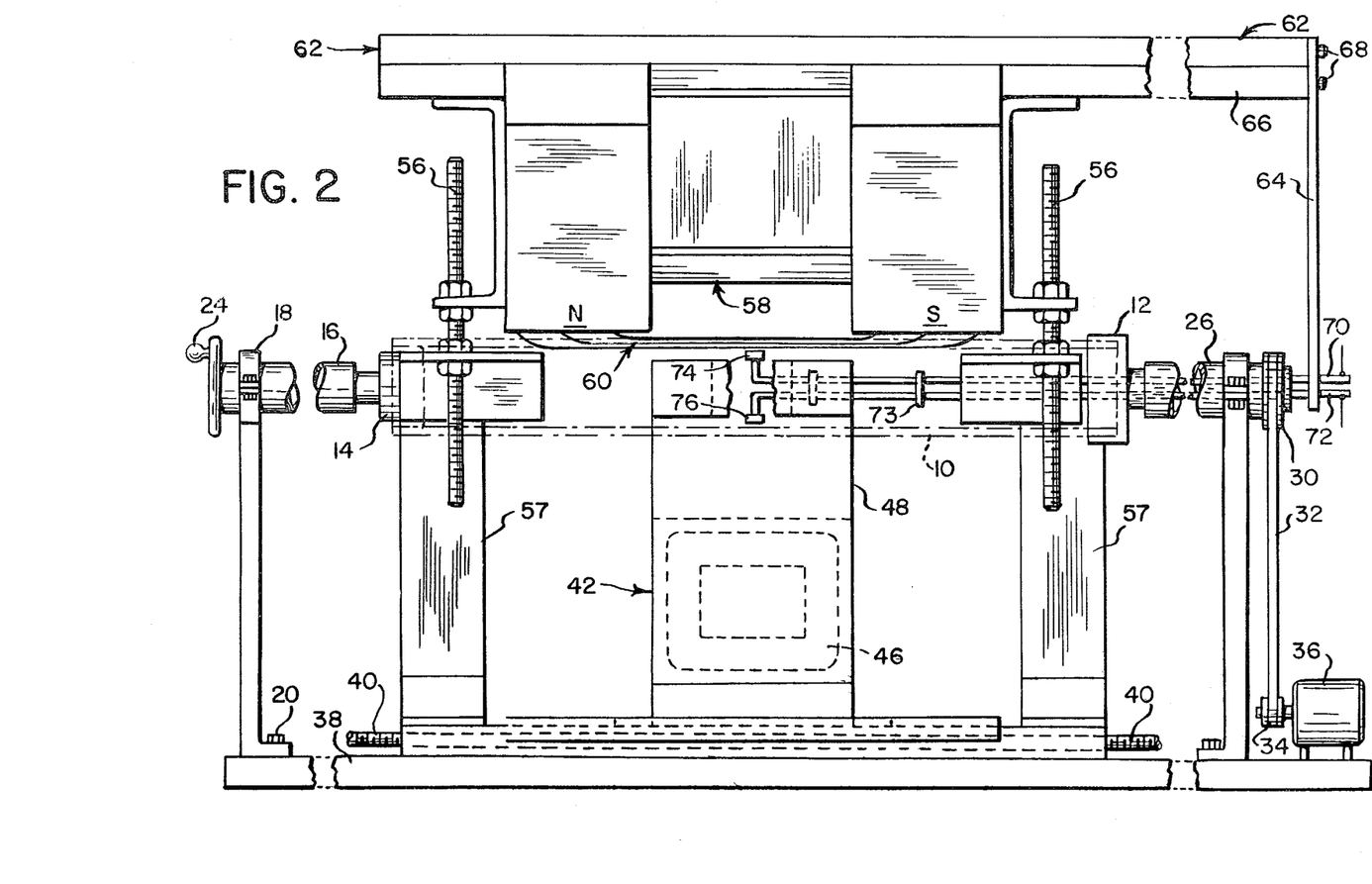
FIG. 2 is a side elevational view of the apparatus of FIG. 1.
Figure 3:
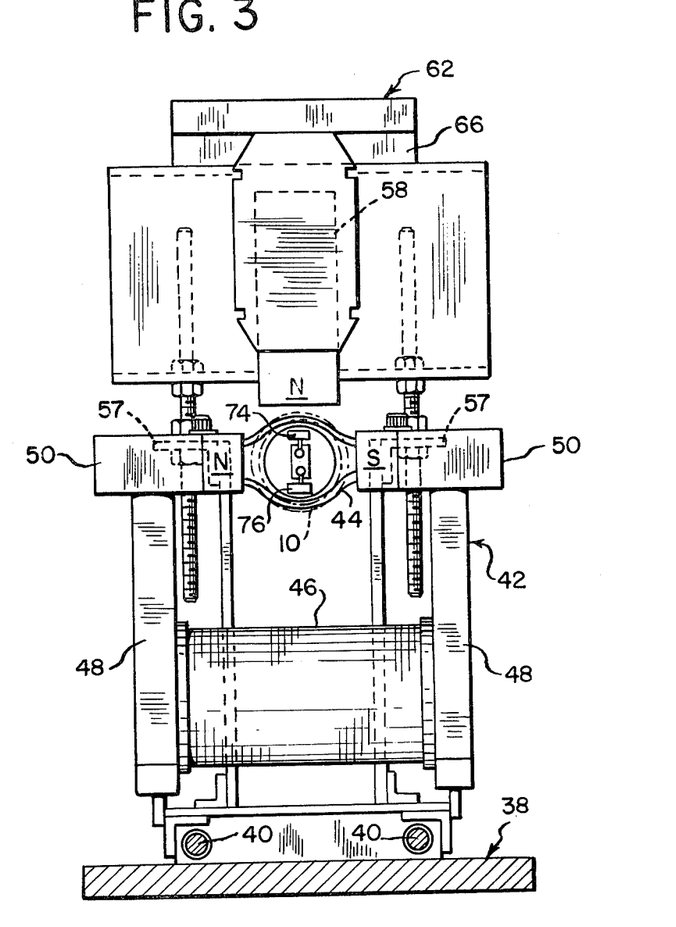
FIG. 3 is an end view of the apparatus of FIG. 1

As may be more fully appreciated by referring also to FIGS. 2 and 3 the important test components of the apparatus illustrated in FIG. 1 are mounted upon a base member 38 which is capable of being transported in the longitudinal direction of the test object by rotation of screws 40. Such means for providing longitudinal motion is well known in the engine lathe art.

Although a permanent magnet may be used it is preferable to use an electromagnet appearing generally as 42 to generate the required transverse magnetic field. By transverse it is meant a field which is perpendicular to the longitudinal axis of test object 10. The direction followed by the magnetic lines of force of this transverse field is represented by flux lines 44 in FIG. 3. Electromagnet 42 has coil 46, core extension members 48 and pole pieces 50. Pole pieces 50 are configured with slots 52 through which bolts 54 pass (Fig.1). Loosening bolts 54 when the current to coil 46 is turned off permits adjustment of the spacing and position of pole pieces 50 to accomodate test objects of different diameters.

Also mounted to base 38 by means of height adjustment screws 56 which are mounted upon support structures 57 is electromagnet 58. Electromagnet 58 provides a field in the longitudinal direction in test object 10. The general direction which the magnetic lines of forces associated with the longitudinal field follow is represented by flux line 60.

Electromagnet 42 is preferably a high strength magnet of approximately 40,000 ampere turns. It should supply a transverse field which nearly magnetically saturates the test object in the region under test to provide adequate sensitivity for longitudinal defects; that is, defects which extend longitudinally rather than defects which extend circumferentially. Electromagnet 58 may provide a field of moderate intensity, a strength of 5 to 10,000 ampere turns is usually sufficient. When both the transverse and longitudinal fields are present within test object 10, the transverse magnetic field is vectored diagonally in the test object; that is, it is deflected somewhat in the longitudinal direction of the test object. Under these conditions leakage flux is produced from the test region; that is, the region in which the longitudinal and transverse fields intersect for both longitudinal and circumferential defects. It is still possible however for defects with certain orientations or for certain rare helical defects to be missed if the field is vectored diagonally in a direction which is parallel to that of the defect. It is therefore desirable that the current supplied to excite the electromagnet 58 not be constant with time. Preferably an alternating current typically of 60 hertz is supplied to electromagnet 58. This serves to constantly change the direction of the magnetic field in the region of intersection of the transverse and longitudinal fields causing it to alternate between slight deviations to the right and to the left (as referenced in FIG. 1) of the normal transverse direction which is directly between the poles 50 of electromagnet 42 as illustrated by flux lines 44 in FIG. 1.

A horizontal plate 62 mounted on electromagnet 58 extends horizontally to the right of electromagnet 58. A vertical support plate 64 is fastened to plate 62 and structural plate 66 by means of machine screws 68. Extending through holes in the lower portion of vertical support plate 64 are two support rods 70 and 72. Connecting members 73 are provided between rods 70 and 72 to produce a rigid structure which adequately maintains rods 70 and 72 in their proper position. Support rods 70 and 72 extend through the hollow interior of shaft 26 toward the region of transverse magnetization. Support rods 70 and 72 should be formed of a non-magnetic material such as a non-magnetic steel or possibly a rigid non-metallic material. As may be seen with reference to FIG. 2 support rod 70 bends upwardly at its extreme left end to support a sensor 74. Sensor 74 is preferably of the type described in U.S. Pat. No. 3,940,690 to Suhr as previously described. Flux leakage sensor 74 is oriented to respond to flux leakage caused by transverse or circumferential defects and produces minimal response from flux leakage due to longitudinal defects despite the fact that such flux leakage may occur at times during the cycle of the alternating current supplied to electromagnet 58.

Support rod 72 serves to position sensor 76 at a point diametrically opposed from the region in which the longitudinal and transverse fields cross. Thus no vectoring of the transverse field in the region of test object 10 rotating past sensor 76 exists. Sensor 76 has the same characteristics as sensor 74 but is oriented to respond to leakage flux caused by longitudinal defects. Thus sensor 74 provides output signals in response to the presence of leakage flux from the first test region while sensor 76 provides output signals which indicate the presence of flaws in the second test region. These output signals are supplied to separate circuit means responsive to such signals and are of the type well known in the art and indications of transverse and longitudinal defects respectively are produced.

In operation test object 10 is secured in the apparatus and motor 36 is energized to rotate object 10. The rotational speed of motor 36 is carefully controlled so that defects of a given size or of a given flux leakage produce signals of consistent amplitude from probes 74 and 76. In addition, it is desirable that the rotational speed of motor 36 not be integrally related to the frequency of the alternating current supplied to electromagnet 58 so that the probability of missing defects is substantially reduced.

Figure 4:
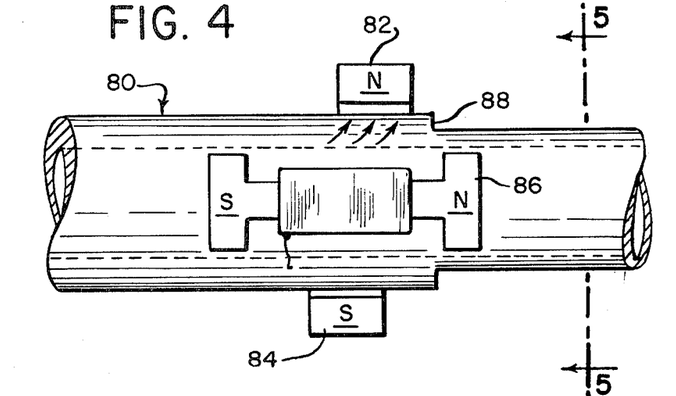
FIG. 4 is a plan diagrammatic view showing the arrangement of components for producing a field which is normally diagonal.

FIG. 4 illustrates an alternate approach to producing diagonal transverse magnetization. A test object 80 has on diametrically opposite sides longitudinally displaced pole pieces 82 and 84. The field produced by this arrangement has a diagonal component due to the longitudinal displacement of the pole pieces. The field may be vectored by the use of electromagnet 86 to which an alternating current may be supplied in a manner similar to electromagnet 58.

Test object 80 has a shoulder 88. Due to a reduction in its outer diameter, the wall thickness of test object 80 is therefore reduced at points to the right of shoulder 88. It would be expected that the field intensity within test object 80 would increase at this point because the same field would be passing through a smaller cross sectional area. This however is not the case due to the fact that the distance between object 80 and the pole faces 82 and 84 increases thus providing additional magnetic reluctance which compensates for the reduction in cross sectional area. This compensation however may not always be entirely adequate and means for providing a substantially uniform field with changes in outer diameter are described below.

Figure 5:
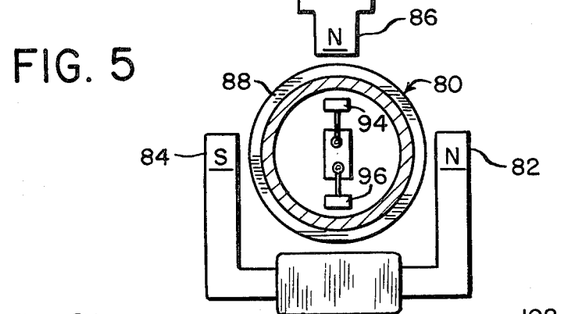
FIG. 5 is a sectional view taken along line 5—5 of FIG. 4.

As illustrated in FIG. 5 sensors 94 and 96 are located internally of test object 80. Generally the flux leakage sensors used in the apparatus of this invention must be mounted so as to be in extremely close proximity to a test object. Therefore if the interior diameter is constant, the sensors are internally mounted while if the exterior diameter is constant they are externally mounted.

It is understood that when shoulder 88 passes by the magnets and sensors that a flux leakage signal will be produced. It thus may under certain circumstances may be difficult to determine whether a flaw indication is being caused by the presence of the shoulder or a flaw located adjacent to the shoulder. According to the apparatus and process of this invention it is merely necessary to terminate relative longitudinal motion to determine whether the flaw is due to the presence of the shoulder or a defect near the shoulder. When relative longitudinal motion is halted, a longitudinal defect will produce a repetitive signal once for every 360° rotation of the test object. A transverse defect will also produce a signal of the same nature except for the very unlikely event in which it extends completely around the circumference of the test object with no longitudinal excursion. The shoulder, however, unless it is not properly formed or changes its longitudinal position around the circumference of the test object will produce no flaw indication while relative longitudinal motion is suspended.

Figure 6:
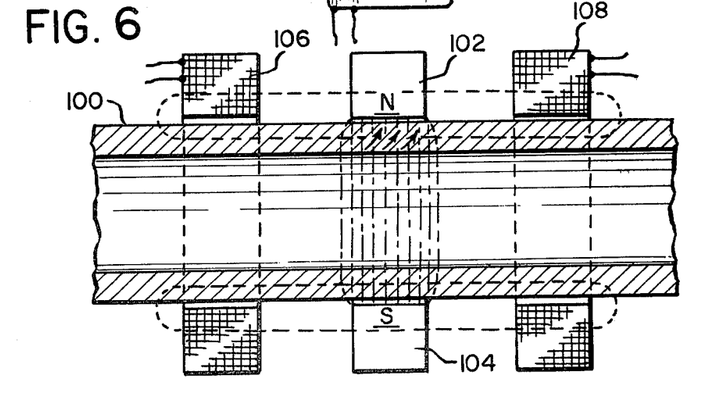
FIG. 6 is a diagrammatic view of the components used in an alternate embodiment of the invention.

In FIG. 6 a transverse magnetic field is induced in test object 100 by electromagnetic pole pieces 102 and 104 in a manner which does not depart from that previously described herein. The longitudinal or vectoring field however is produced by a pair of coils 106 and 108 which have a configuration very similar to Helmholtz coils. An alternating current may be supplied to coils 106 and 108 which of course must be properly phased so that the magnetic field generated by each is not cancelled by the other. For simplicity no sensors have been shown.

Figure 7:
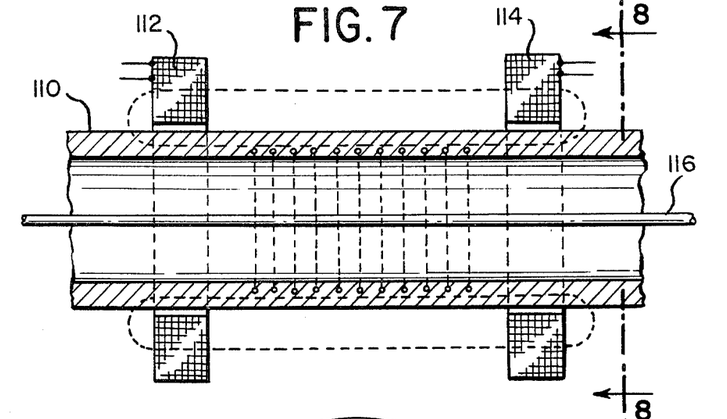
FIG. 7 is a diagrammatic view of the components used in an another embodiment of the invention.
Figure 8:
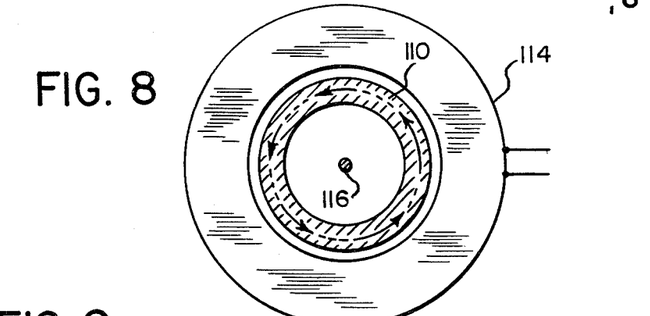
FIG. 8 is taken along line 8—8 of FIG. 7.

In FIG. 7 the longitudinal or vectoring field is introduced into test object 110 by coils 112 and 114 in a manner identical to that illustrated in FIG. 6. To generate the transverse field however a strong current is passed through a central conductor 116 extending along the longitudinal axis of test object 110. The transverse field produce in this manner extends continuously around the circumference of test object 110 as may be appreciated by reference to FIG. 8. The field thus extends from right to left in the top of object 110 and from left to right through the bottom of object 110. This difference is of no consequence, it is for test purposes. It is understood that the apparatus of the invention illustrated in FIGS. 1 through 3 could be modified so that a central conductor extending along the longitudinal axis of the test object could be provided. It then might be advantageous to locate the sensors externally of the test object providing that the external diameter is constant.

Figure 9:
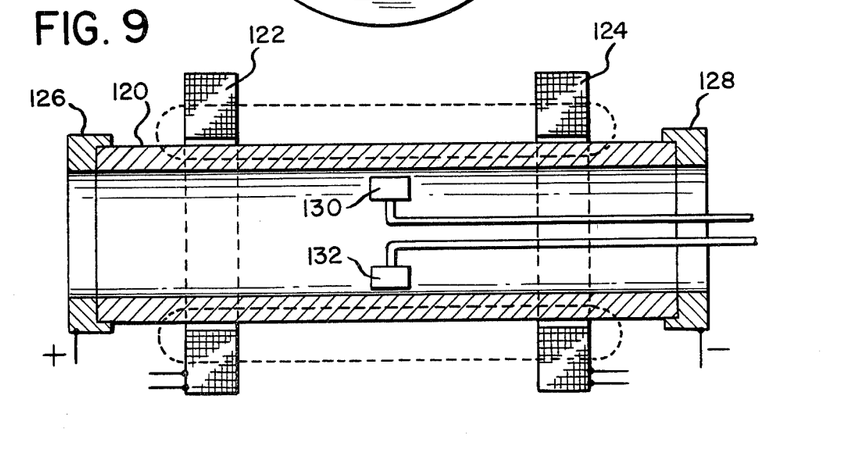
FIG. 9 is a diagrammatic view of an additional embodiment of the invention.

In FIG. 9 the longitudinal or vectoring field in test object 120 is supplied in a manner identical to that shown in FIG. 7 by coils 122 and 124. Instead of running current through a central conductor disposed on the longitudinal axis of the test object, current is run through the test object itself. Contact rings 126 and 128 are supplied to provide intimate electrical connection to the test object. Rings 126 and 128 could be electrically fed as slip rings if required. It should be understood that a test object 120 is mounted in the apparatus of the invention described above. It will be necessary to electrically isolate either external clamping means 12 or internal support means 14 in order to prevent current supply from being divided between test object 120 and the electrically conductive structure of the apparatus.

In the arrangement shown in FIG. 9 both sensors no matter how positioned around the diameter of test object 120 will be adjacent an area having a vectored field. Sensor 130 may however be responsive to flux leakage caused by circumferential defects while sensor 132 is responsive to flux leakage caused by longitudinal defects in a manner indicated above.

Figure 10:
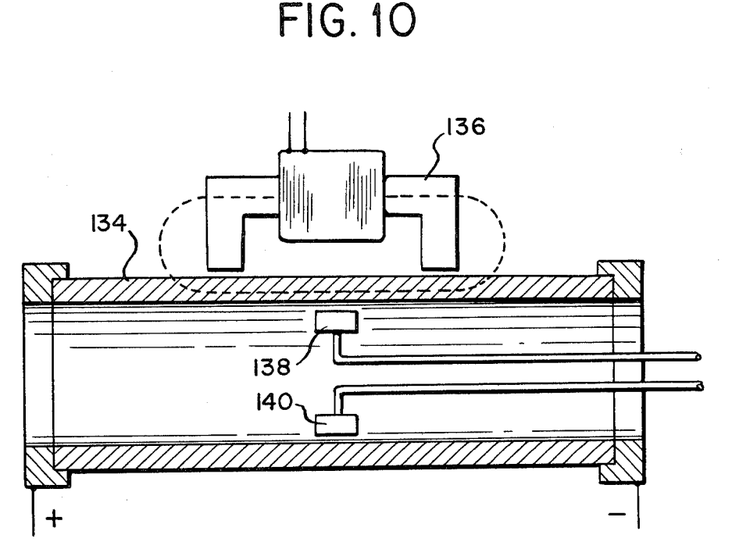
FIG. 10 is a diagrammatic view of a further embodiment of the invention.

In FIG. 10 the transverse field in test object 134 is produced as in FIG. 9 but an electromagnet 136 is used to produce the vectoring field. Sensors 138 and 140 respond to circumferential and longitudinal defects in the test object respectively.

Figure 11:
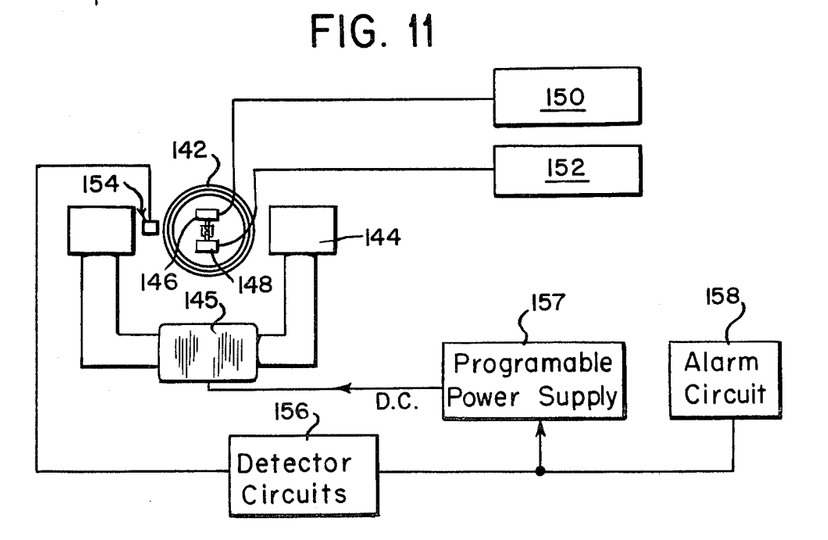
FIG. 11 is a block diagram of an apparatus according to the invention particularly adapted to detect flaws in objects with varying wall thicknesses.

While the apparatus described above and the possible implementation by various arrangements of components and magnetic field generating means described above are perfectly adequate for producing a practical device in many situations, it is often necessary especially in cases where the diameter of a test object changes and a variation in wall thickness results, to provide a means for correcting the intensity of the transverse field to produce uniform indication outputs for flaws of relatively similar severity at different locations within the test object. In FIG. 11 test object 142 shown in end view has various shoulders. Electromagnet 144 provides the transverse field. A longitudinal field is also provided by an electromagnet not shown in FIG. 11. Sensors 146 and 148 provide flux leakage output signals to two flaw indicating circuits 150 and 152 which may be of the type disclosed in the above referenced U.S. Pat. No. 3,940,690. A flux intensity sensor 154 is positioned so that in combination with suitable detector circuitry 156 it provides an indirect measure of the flux density within test object 142. Its output is fed to a programmable power supply which serves as a power source for the coil associated with electromagnet 144. It is thus possible to energize electromagnet 144 and by incrementally changing the relative longitudinal positions of test object 142 and the test apparatus provide information to the programmable power supply to correct the current supplied to the coil 145 of the electromagnet 144 to correct the intensity of the field within test object 142 so it is substantially uniform throughout the relative longitudinal travel of the test object in the test apparatus. Occassionally however due to variations in material or possibly test conditions even this correction will not be adequate to keep the field within predetermined bounds. The output of the detector circuit 156 can thus be supplied to an alarm circuit 158 which provides an indication when the flux intensity within object 142 is outside a predetermined range producing flaw indications which are of questionable validity.

For reasons not entirely understood the vectoring of the transverse field in a test object by a longitudinal field reduces the magnitude of flux leakage signals which are associated with a weld zone in the test object.

It should be understood that other arrangements than those disclosed in FIGS. 1 through 3 can be used to provide relative motion between the test object and the test apparatus. In FIGS. 1 through 3 the test object is stationary while the test apparatus is longitudinally displaced as the object rotates thus scanning the test object. It is also possible and especially desirable with longer test objects, where the sensor support rods would be of an impractical length if internally located, to hold the magnet and sensors stationary and to move the test object past a fixed test station. Under these circumstances it is not uncommon to have the magnets and sensors rotating while the test object does not rotate. It is also possible for the test object to translate and rotate past a fixed test station.

Various other modifications of the invention in addition to those described herein will become apparent to one skilled in the art from the above drawings and description which have been offered by way of illustration only and not in limitation of the invention, the scope of which is defined in the appended claims.

I claim:

1. Apparatus for providing simultaneous magnetic flux leakage detection of transverse and longitudinal flaws in an object relatively moving longitudinally and rotationally with respect to said apparatus, comprising:
   (a) means for producing a transverse magnetic field in said object;
   (b) means for producing a longitudinal magnetic field intersecting a portion of said transverse magnetic field to produce a vectored magnetic field in a first test region of said object;
   (c) first magnetic flux sensor means for providing output signals in response to the presence of leakage flux produced by transverse flaws subjected to said vectored magnetic field in said first test region;
   (d) second magnetic flux sensor means for providing output signals in response to the presence of leakage flux produced by longitudinal flaws in a second test region of said object subjected to said transverse magnetic field;
   (e) first circuit means responsive to the output signals of said first magnetic flux sensor means for indicating detected transverse flaws in said object; and
   (f) second circuit means responsive to the output signals of said second magnetic flux sensor for indicating detected longitudinal flaws in said object.

2. The apparatus of claim 1 in which said means for producing said transverse magnetic field produces a field intensity just below that necessary to cause magnetic saturation of said object.

3. The apparatus of claim 1 wherein an electromagnet is used to generate the transverse magnetic field and a dedicated magnetic field sensor is positioned to sense the strength of the transverse magnetic field and produce a signal which controls the energizing current supplied to the electromagnet to thereby provide a substantially constant transverse magnetic field in said object as wall thickness of said object changes along said object.

4. The apparatus of claim 3 further comprising means for providing an indication when transverse magnetic field intensity falls outside a predetermined desired range of values.

5. The apparatus of any one of claims 1 through 4 in which the means for producing said longitudinal magnetic field is energized by an alternating current source.

6. The apparatus of claim 1 further comprising drive means for rotationally and longitudinally moving the test object relative to said apparatus including means for interrupting longitudinal movement of the object relative to the test apparatus while continuing rotational movement.

7. The apparatus in accordance with any of claims 1 through 4 wherein the pole pieces of the means for producing a transverse magnetic field in the object are skewed relative to field lines normal to the longitudinal magnetic field.

8. A process for magnetically detecting flaws in a rotationally and longitudinally moving test object comprising the steps of:
    (a) generating a magnetic field in the test object transverse to the direction of longitudinal movement;
    (b) generating a longitudinal magnetic field intercepting said transverse magnetic field in a first test region of said object to produce a vectored magnetic field therein;
    (c) sensing leakage flux produced by transverse flaws subjected to said vectored magnetic field in said first test region and producing an output signal in response thereto;
    (d) sensing leakage flux produced by longitudinal flaws in said object in a second test region subjected only to said transverse field and producing an output signal in response thereto; and
    (e) processing said output signals to simultaneously produce indication of both tranverse and longitudinal flaws in said object.

* * * * *